Figure 1A:
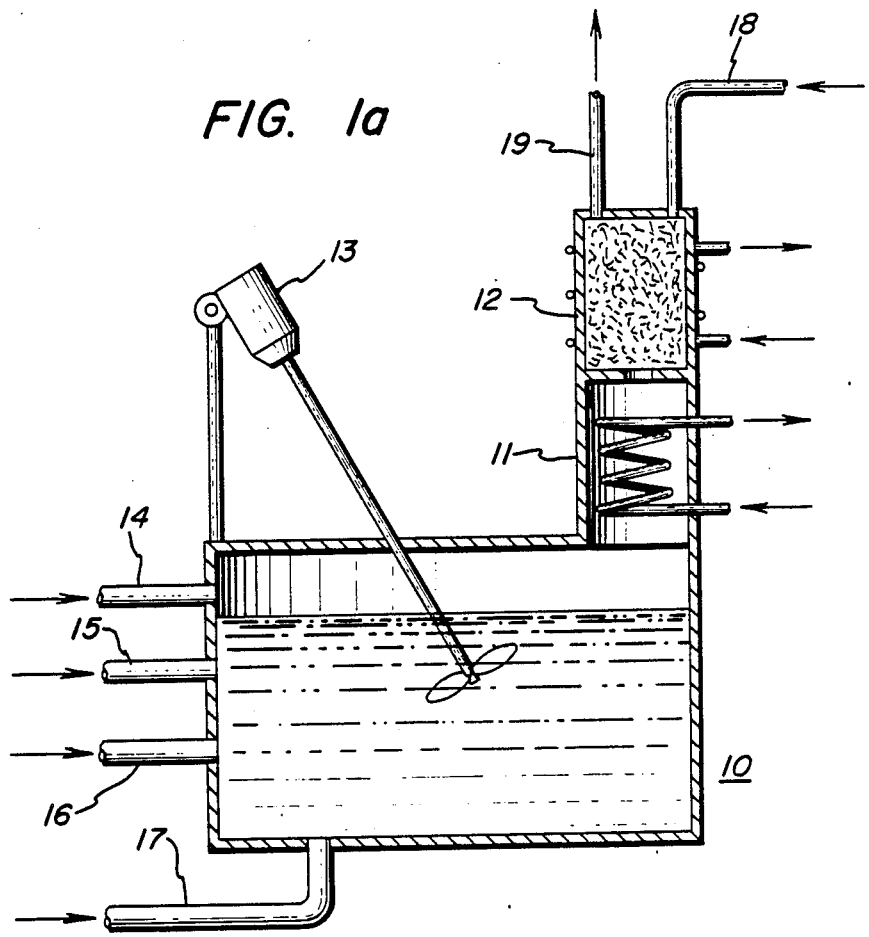

United States Patent [19]
Silva

[11] Patent Number: 4,701,544
[45] Date of Patent: Oct. 20, 1987

[54] METHOD FOR MAKING REACTION PRODUCTS OF PHOSGENE AND DIHYDRIC PHENOL

[75] Inventor: James M. Silva, Clifton Park, N.Y.

[73] Assignee: General Electric Company, Schenectady, N.Y.

[21] Appl. No.: 892,549

[22] Filed: Aug. 4, 1986

[51] Int. Cl.$^4$ ............................................. C07C 68/00
[52] U.S. Cl. ................................. 558/281; 558/274; 558/280; 558/283; 558/284
[58] Field of Search ............... 558/281, 280, 281, 284, 558/274, 283

[56] References Cited

U.S. PATENT DOCUMENTS 2,476,637  7/1949  Strain et al. ..................... 558/281 X
2,764,607  9/1956  Hieserman et al. ................. 558/281
3,910,983  10/1975 Merkel et al. ....................... 558/281

OTHER PUBLICATIONS

Kondratenko et al., Chem Abst., vol. 93, #15000g, (1980).
Caraculescu et al., Chem. Abst., vol. 93, #47751f, (1980).
Block, Chem. Abst., vol. 86, #95131f, (1977).

Primary Examiner—James H. Reamer
Attorney, Agent, or Firm—William A. Teoli; James C. Davis, Jr.; James Magee, Jr.

[57] ABSTRACT

A method is provided for making reaction products of phosgene and dihydric phenol, such as bischloroformates and polycarbonates utilizing a reactor with an overhead condenser. Reduced phosgene blow-by is achieved by using an absorber for phosgene which is connected in series to the overhead condenser.

6 Claims, 4 Drawing Figures

METHOD FOR MAKING REACTION PRODUCTS OF PHOSGENE AND DIHYDRIC PHENOL

BACKGROUND OF THE INVENTION

Prior to the present invention, reactions of a dihydric phenol and phosgene to make the corresponding bischloroformate of the dihydric phenol, or polycarbonate, often resulted in "phosgene blow-by", that is the loss of phosgene from the phosgenation reactor condenser vent. Various efforts have been used to eliminate the loss of phosgene into the environment due to its toxic properties. One procedure is to vent the phosgene into a scrubber containing an organic amine, as shown by U.S. Pat. No. 4,493,818. A preferred procedure to minimize phosgene blow-by would be to salvage the phosgene instead of destroying it, in view of economic considerations.

The present invention is based on my discovery that phosgene loss due to blow-by can be reduced by passing the vent stream from the overhead condenser, normally used in batch or continuous reactors, to an absorber fed with an organic solvent, such as methylene chloride followed by the return of the phosgene-containing solvent to the reactor.

STATEMENT OF THE INVENTION

A method is provided for making phosgene-dihydric phenol reaction products in condenser-vented reactors whereby reduced phosgene blow-by is achieved, comprising (1) effecting reaction between a dihydric phenol and phosgene under interfacial reaction conditions in the presence of an organic solvent, and (2) venting volatiles resulting from (1) through a condenser, which is series connected to an organic solvent-fed absorber, and (3) conveying the phosgene-containing solvent from the absorber to the reactor.

Some of the dihydric phenols which can be utilized in the practice of the present invention make dihydric phenol reaction products are, for example,
Resorcinol
4-Bromoresorcinol
Hydroquinone
4,4'-Dihydroxybiphenyl
1,6-Dihydroxynaphthalene
2,6-Dihydroxynaphthalene
Bis(4-hydroxyphenyl)methane
Bis(4-hydroxyphenyl)diphenylmethane
Bis(4-hydroxyphenyl)-1-naphthylmethane
1,1-Bis(4-hydroxyphenyl)ethane
1,2-Bis(4-hydroxyphenyl)ethane
1,1-Bis(4-hydroxyphenyl)-1-phenylethane
2,2-Bis(4-hydroxyphenyl)propane ("bisphenol A")
2-(4-Hydroxyphenyl)-2-)3-hydroxyphenyl)propane
2,2-Bis(4-hydroxyphenyl)butane
1,1-Bis(4-hydroxyphenyl)isobutane
1,1-Bis(4-hydroxyphenyl)cyclohexane
1,1-Bis(4-hydroxyphenyl)cyclododecane
Trans-2,3-bis(4-hydroxyphenyl)-2-butene
2,2-Bis(4-hydroxyphenyl)adamantane
α,α'-Bis(4-hydroxyphenyl)toluene
Bis(4-hydroxyphenyl)acetonitrile
2,2-Bis(3-methyl-4-hydroxyphenyl)propane
2,2-Bis(3-ethyl-4-hydroxyphenyl)propane
2,2-Bis(3-n-propyl-4-hydroxyphenyl)propane
2,2-Bis(3-isopropyl-4-hydroxyphenyl)propane
2,2-Bis(3-sec-butyl-4-hydroxyphenyl)propane
2,2-Bis(3-t-butyl-4-hydroxyphenyl)propane
2,2-Bis(3-cyclohexyl-4-hydroxyphenyl)propane
2,2-Bis(3-allyl-4-hydroxyphenyl)propane
2,2-Bis(3-methoxy-4-hydroxyphenyl)propane
2,2-Bis(3,5-dimethyl-4-hydroxyphenyl)propane
2,2-Bis(2,3,5,6-tetramethyl-4-hydroxyphenyl)propane
2,2-Bis(3-5-dichloro-4-hydroxyphenyl)propane
2,2-Bis(3,5-dibromo-4-hydroxyphenyl)propane
2,2-Bis(2,6-dibromo-3,5-dimethyl-4-hydroxyphenyl)propane
α,α-Bis(4-hydroxyphenyl)toluene
α,α,α',α'-Tetramethyl-α,α'-bis(4-hydroxyphenyl)-p-xylene
2,2-Bis(4-hyroxyphenyl)hexafluoropropane
1,1-Dichloro-2,2-bis(4-hydroxyphenyl)ethylene
1,1-Dibromo-2,2-bis(4-hydroxyphenyl)ethylene
1,1-Dichloro-2,2-bis(5-phenoxy-4-hydroxyphenyl)ethylene
4,4'-Dihydroxybenzophenone
3,3-Bis(4-hydroxyphenyl)-2-butanone
1,6-Bis(4-hydroxyphenyl)-1,6-hexanedione
Bis(4-hydroxyphenyl) ether
Bis(4-hydroxyphenyl) sulfide
Bis(4-hydroxyphenyl) sulfoxide
Bis(4-hydroxyphenyl) sulfone
Bis(3,5-dimethyl-4-hydroxyphenyl) sulfone
9,9-Bis(4-hydroxyphenyl)fluorene
2,7-Dihydroxypyrene
6,6'-Dihydroxy-3,3,3',3'-tetramethylspiro(bis)indane ("spirobiindane bisphenol")
3,3-Bis(4-hydroxyphenyl)phthalide
2,6-Dihydroxydibenzo-p-dioxin
2,6-Dihydroxythianthrene
2,7-Dihydroxyphenoxathiin
2,7-Dihydroxy-9,10-dimethylphenazine
3,6-Dihydroxydibenzofuran
3,6-Dihydroxydibenzothiophene
2,7-Dihydroxycarbazole
4,4'-dihydroxy-diphenyl-1,1-butane
4,4'-dihydroxy-diphenyl-1,1-isobutane
4,4'-dihydroxy-diphenyl-1,1-cyclopentane
4,4'-dihydroxy-diphenyl-1,1-cyclohexane
4,4'-dihydroxy-diphenyl-phenyl methane
4,4'-dihydroxy-diphenyl-2-chlorophenyl methane
4,4'-dihydroxy-diphenyl-2,4-dichlorophenyl methane
4,4'-dihydroxy-diphenyl-p-isopropylphenyl methane
4,4'-dihydroxy-diphenylnaphthyl methane
4,4'-dihydroxy-diphenyl-2,2-propane
4,4'-dihydroxy-3-methyl-diphenyl-2,2-propane
4,4'-dihydroxy-3-cyclohexyl-diphenyl-2,2-propane
4,4'-dihydroxy-3-methoxy-diphenyl-2,2-propane
4,4'-dihydroxy-3-isopropyl-diphenyl-2,2-propane
4,4'-dihydroxy-3,3'-dimethyl-diphenyl-2,2-propane
4,4'-dihydroxy-3,3'-dichloro-diphenyl-2,2-propane
4,4'-dihydroxy-diphenyl ether Phosgene-dihydric phenol reaction products which can be made in accordance with the practice of the present invention are, for example, monochloroformates and bischloroformates of the dihydric phenols, mixtures of oligomeric carbonate mono and bischloroformate of the dihydric phenols, and polycarbonate polymers of the dihydric phenols.

In general, the bischloroformate compositions prepared by the method of this invention consist essentially of compounds having the formula

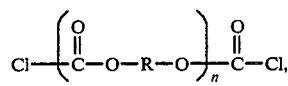

wherein R is a divalent $C_{(6-14)}$ aromatic organic radical and n is at least 1.

In preparing polycarbonate polymers, the reactant is typically a dihydric phenol as described above. Reaction takes place in the presence of an interfacial polycondensation catalyst to generate the polymer. The most preferred reactant is bisphenol-A. The phosgene flow rate is typically in the range of 0.01 to 0.2 equivalents per equivalent of reactant per minute. The temperature is preferably in the range of 10°–40° C. and most preferably 20°–40° C. when producing polycarbonates. Pressures of about 1 atmosphere are preferred.

Organic solvents which can be used in the practice of the present invention are, for example, aliphatic hydrocarbons such as hexane and n-heptane; chlorinated aliphatic hydrocarbons such as methylene chloride, chloroform, carbon tetrachloride, dichloroethane, trichloroethane, tetrachloroethane, dichloropropane and 1,2-dichloroethylene; aromatic hydrocarbons such as benzene, toluene and xylene; substituted aromatic hydrocarbons such as chlorobenzene, o-dichlorobenzene, the chlorotoluenes, nitrobenzene and acetophenone; and carbon disulfide. The chlorinated aliphatic hydrocarbons, especially methylene chloride, are preferred. Although it is not essential for the reaction organic solvent and the absorber organic solvent to be identical, it is often simpler to employ the same solvent for both the reactor and absorber.

The reaction pH is controlled using an aqueous alkali metal hydroxide or alkaline earth metal hydroxide such as sodium hydroxide, potassium hydroxide or calcium hydroxide. Sodium and potassium hydroxides, and especially sodium hydroxide, are preferred because of their relative availability and low cost.

Figure 1B:
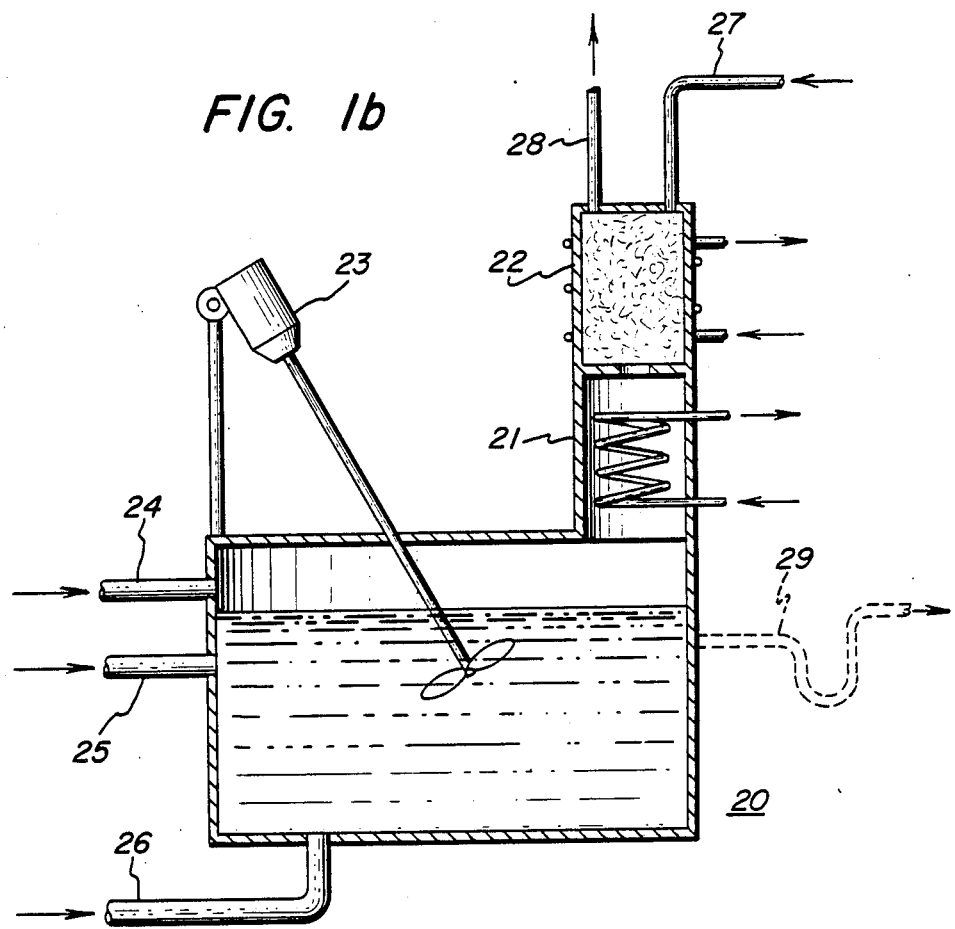

In order that those skilled in the art will be better able to understand the practice of the present invention, reference is made to the drawings, where FIG. 1a and FIG. 1b are schematic diagrams of reactors having a condenser and a vertically connected absorber in series wherein the solution leaving the absorber passes through the condenser prior to entering the reactor.

Figure 2A:
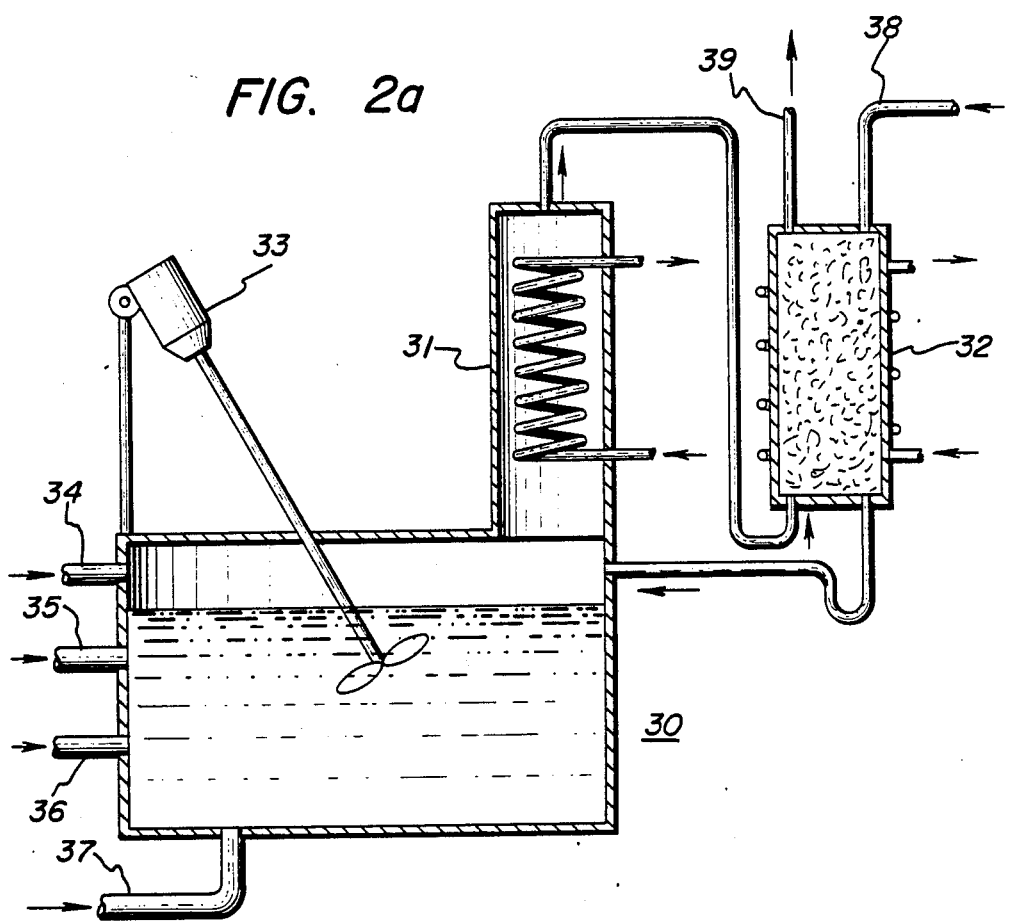
Figure 2B:
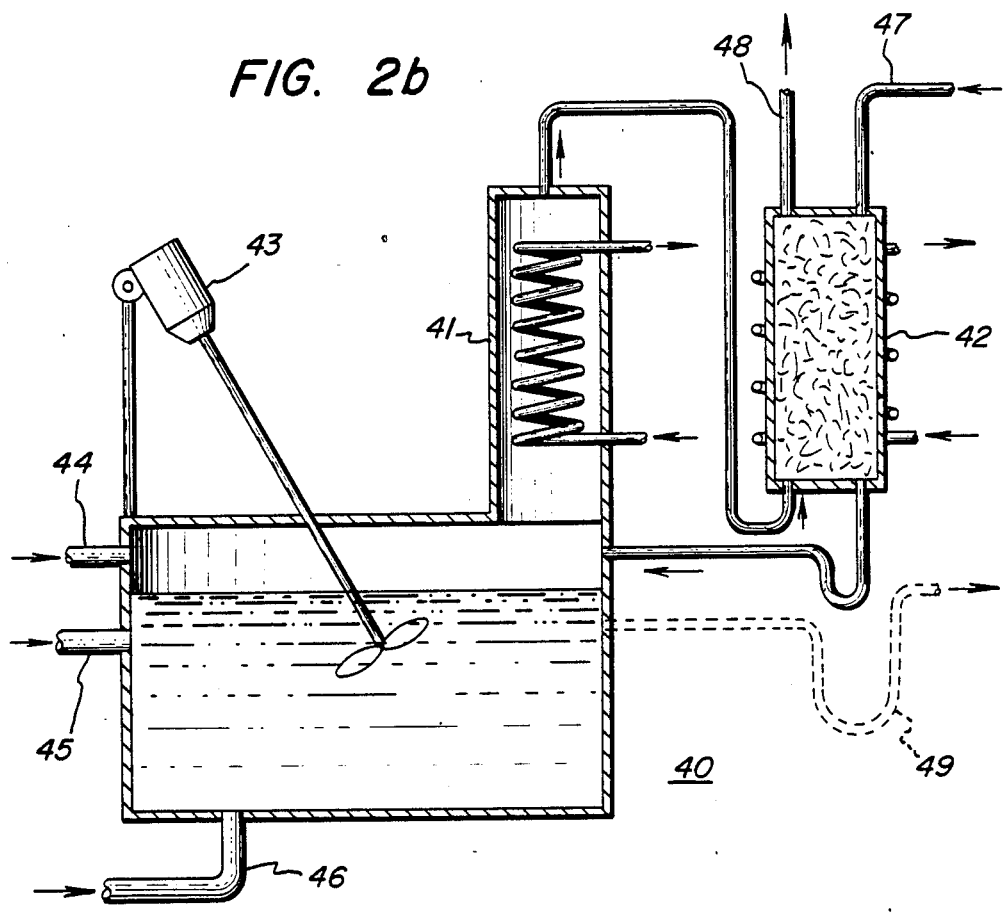

FIGS. 2a and 2b are schematic diagrams of reactors having a condenser and absorber connected in series with respect to the vapor flow, but the solution leaving the absorber enters the reactor directly.

There is shown more particularly in FIG. 1a a batch reactor for making polycarbonate at 10 having a condenser at 11 and an absorber at 12. A stirrer for the reactor is shown at 13, while a BPA feed port is shown at 14, an NaOH-water feed port is shown at 15, a chain stopper and amine catalyst feed port is shown at 16, and a phosgene feed port is shown at 17. An organic solvent such as methylene chloride is introduced at 18 to absorb phosgene not condensed by condenser 11, while a vent is shown at 19.

In FIG. 1b, there is shown a continuous reactor at 20 for making bischloroformates, a condenser at 21 and an absorber at 22. A stirrer for the reactor is shown at 23, a BPA feed port is shown at 24, and a NaOH/H₂O feed port is shown at 25. There is further shown a phosgene feed port at 26, a methylene chloride feed port at 27, a vent at 28 and a port for liquid product overflow with a liquid seal at 29.

In FIG. 2a, there is shown a batch reactor for making polycarbonate at 30, a condenser at 31 and an absorber at 32. A stirrer is shown at 33, a BPA feed port is shown at 34, an NaOH/water feed port is shown at 35, and a port for the introduction of tri-organic amine catalyst and chain-stopper is shown at 36. A phosgene feed port is shown at 37, while an organic solvent such as methylene chloride can be introduced at 38 and a vent is shown at 39.

There is shown in FIG. 2b, a continuous reactor for making bischloroformates at 40, a condenser at 41 and an absorber at 42. A stirrer for the reactor is shown at 43, a BPA feed port is shown at 44 and a NaOH/H₂O feed port at 45. There is further shown a phosgene feed port at 46, a methylene chloride feed port at 47, a vent at 48 and a port for liquid product overflow with a liquid seal at 49.

In accordance with the practice of one form of the invention, a mixture of the dihydric phenol, water, alkali metal hydroxide, and organic solvent is agitated at a temperature in the range of from 15° C. to 50° C. while phosgene is continuously added to the reactor. In instances where bischloroformate of the dihydricphenol is manufactured, a proportion of from 1.5 moles to 3 moles of phosgene per mole of dihydricphenol is utilized. Alternatively, in instances where polycarbonate is desired, a proportion of 1.01 moles to 1.5 moles of phosgene per mole of dihydric phenol is used. In addition, 0.8 to 2 mols of a tri-organic amine, such as triethylamine, per 100 mols of dihydric phenol and a suitable chainstopper, for instance phenol, is added in proportion of from 1 to 10 mols chainstopper per 100 mol dihydric phenols will provide effective results.

For bischloroformate synthesis, a proportion of 1 to 4 equivalents of alkali metal hydroxide (or alkaline earth hydroxide) per mol dihydric phenol can be utilized. Preferably, there can be used from 2 to 3 equivalents of alkali metal hydroxide per mol of the dihydric phenol. For polycarbonate synthesis, the proportion of 2–4 equivalents of alkali metal hydroxide (or alkaline earth metal hydroxide) per mol dihydric phenol and preferably 2–3 equivalents is effective.

Sufficient water and organic solvent can be employed to provide a product concentration of from 1 to 12% based on the weight of total solvent.

A proportion of from 0.25 to 1.5 parts of water per part of organic solvent such as methylene chloride, and preferably from 0.3 to 1 part water per part organic solvent by volume can be used.

The reactor may be run either batchwise, in which the reactor is initially charged with all ingredients except phosgene and most of the aqueous base solution, which are added during the course of the reaction (5 min.–2 hrs.), or continuously, in which all ingredients are added continuously (either as continuous streams or portionwise) and product is removed continuously.

In order that those skilled in the art will be better able to practice the present invention, the following examples are given by way of illustration and not by way of limitation. All parts are by weight.

EXAMPLE 1

A 500 ml Morton flask was modified by fitting it with an overflow device, a condenser/absorber, a paddle stirrer, a thermometer, and a pH probe. There was also connected to the Morton flask, separate feed pumps for 5 molar NaOH and methylene chloride. The resulting reactor was immersed in a water bath for temperature control. 5 molar NaOH solution was introduced directly into the reactor for pH control.

The absorber section of the condenser/absorber was a short (3" high ×1" diameter) glass section packed with stainless steel mesh mounted directly beneath the condenser. The assembled apparatus was operated as a continuous stirred tank reactor with methylene chloride added continuously to the top of the condenser to precool the methylene chloride. The condenser was cooled with 40° F. coolant. The condenser/absorber mounted on top of the reactor also allowed for the venting of gas from the condenser to an aqueous 5 molar solution of sodium hydroxide to effect phosgene destruction. The reactor was operated initially in a batch mode having no methylene chloride added to the absorber/condenser followed by continuous operation at two different phosgene flow rates with methylene chloride continuously added to the top of the condenser/absorber.

During batch operation, the reactor was initially charged with 15 grams of bisphenol-A, 130 ml of methylene chloride, and 20 ml of distilled water. Phosgene gas was added at 3.3 grams/minute for 9 minutes, and 5 M NaOH was added to maintain the pH within the range 2–5. After 9 minutes of batch operation, the reactor was operated in the continuous mode. During continuous operation, the reactor was operated as a single continuous stirred tank reactor after the initial batch startup. Phosgene was added continuously at 3.3 grams/minute for 15 minutes followed by operation at 5 grams/minute for 10 minutes. Methylene chloride was added to the absorber at 30 cc/minute and BPA was added proportion-wise at an average of 6 grams/minute. The residence time in the reactor was 5 minutes.

Product from the reactor was quenched with an excess of triethylamine and phenol and analyzed by HPLC to provide the following composition of oligomeric carbonate chloroformates:

| | Mol Monomeric Unit/Liter $CH_2Cl_2$ Solution | | |
|---|---|---|---|
| | Batch | Composite 1 3.3 gm/min $COCl_2$ | Composite 2 5.0 gm/min $COCl_2$ |
| BPA | 0.0098 | 0.048 | 0.0459 |
| $COCl_2$ | 1.398 | 0.074 | 0.2356 |
| BPA-Monochloroformate | 0.062 | 0.087 | 0.106 |
| BPA-Bischloroformate | 0.541 | 0.438 | 0.441 |
| Dimer-Monochloroformate | 0.077 | 0.114 | 0.109 |
| 2-Bischloroformate | 0.078 | 0.145 | 0.167 |
| 3-Bischloroformate | 0.013 | 0.048 | 0.049 |
| 4-Bischloroformate | 0.005 | 0.016 | 0.014 |
| 5-Bischloroformate | 0.002 | 0.004 | 0.004 |
| Total mol monomeric unit: liter $CH_2Cl_2$ | 0.79 | 0.90 | 0.94 |

The above reaction was run at reactor temperatures maintained below 34° C. No bubbling was observed from the dip tube immersed in the vent scrubber flask containing 5M NaOH. It was further found that in instances where the same reaction was run without the absorber, phosgene was observed bubbling into the sodium hydroxide scrubber.

EXAMPLE 2

The reactor was set up as described in Example 1, except that the condenser/absorber was mounted above the reactor and the absorber section was mounted above the condenser. The reactor was charged with 250 ml of methylene chloride, 500 ml of water, 114 grams of bisphenol-A, 0.5 grams of triethylamine catalyst and 2.8 grams of phenol chain-stopper. Phosgene was introduced at 3.96 grams/minute for 15 minutes and the pH of the mixture was maintained at 11 by use of a 50% by weight of sodium hydroxide and 17 cc/minute methylene chloride was introduced to the top of the absorbed. A quantitative yield of polycarbonate was obtained. It was further found that phosgene escaped into the sodium hydroxide scrubber when the absorber was not used.

Although the above examples are directed to only a few of the very many variables which can be utilized in the practice of the method of the present invention, it should be understood that the method of the present invention directed to the use of a much broader variety of dihydric phenols, alkali metal hydroxides, organic solvents, and reaction conditions as set forth in the description preceding these examples.

What is claimed and sought to be protected by Letters Patent of the United States is as follows:

1. A method for making phosgene-dihydric phenol reaction products in a condenser/absorber-vented reactor under interfacial reaction conditions whereby reduced phosgene blow-by is achieved, comprising,
    (1) effecting reaction between a dihydric phenol and phosgene under interfacial reaction conditions in the presence of aqueous base, water, and methylene chloride at a temperature in the range of between 10°–40° C.,
    (2) venting phosgene-containing volatiles from (1) through the condenser connected to a methylene chloride fed absorber, and
    (3) returning phosgene-containing methylene chloride from the absorber to the reactor, where there is used a volume ratio of water to methylene chloride having a value of from 0.25 to 1.5, which is sufficient to provide a product concentration of from 1 to 12%, based on the total weight of solvent.

2. A method in accordance with claim 1, where the dihydric phenol is bisphenol-A.

3. A method in accordance with claim 1, where the dihydric phenol reaction product is polycarbonate.

4. A method in accordance with claim 1, where the dihydric phenol reaction product is a bischloroformate or an oligomeric carbonate bischloroformate mixture.

5. A method in accordance with claim 1, where the condenser and the absorber are connected in parallel, whereby the solution enters the reactor directly through a liquid seal.

6. A method in accordance with claim 1, where the absorber is vertically connected above the condenser.

* * * * *